Feb. 11, 1964 C. FISCHER Plant Pat. 2,361
GLADIOLUS PLANT
Filed Dec. 18, 1962
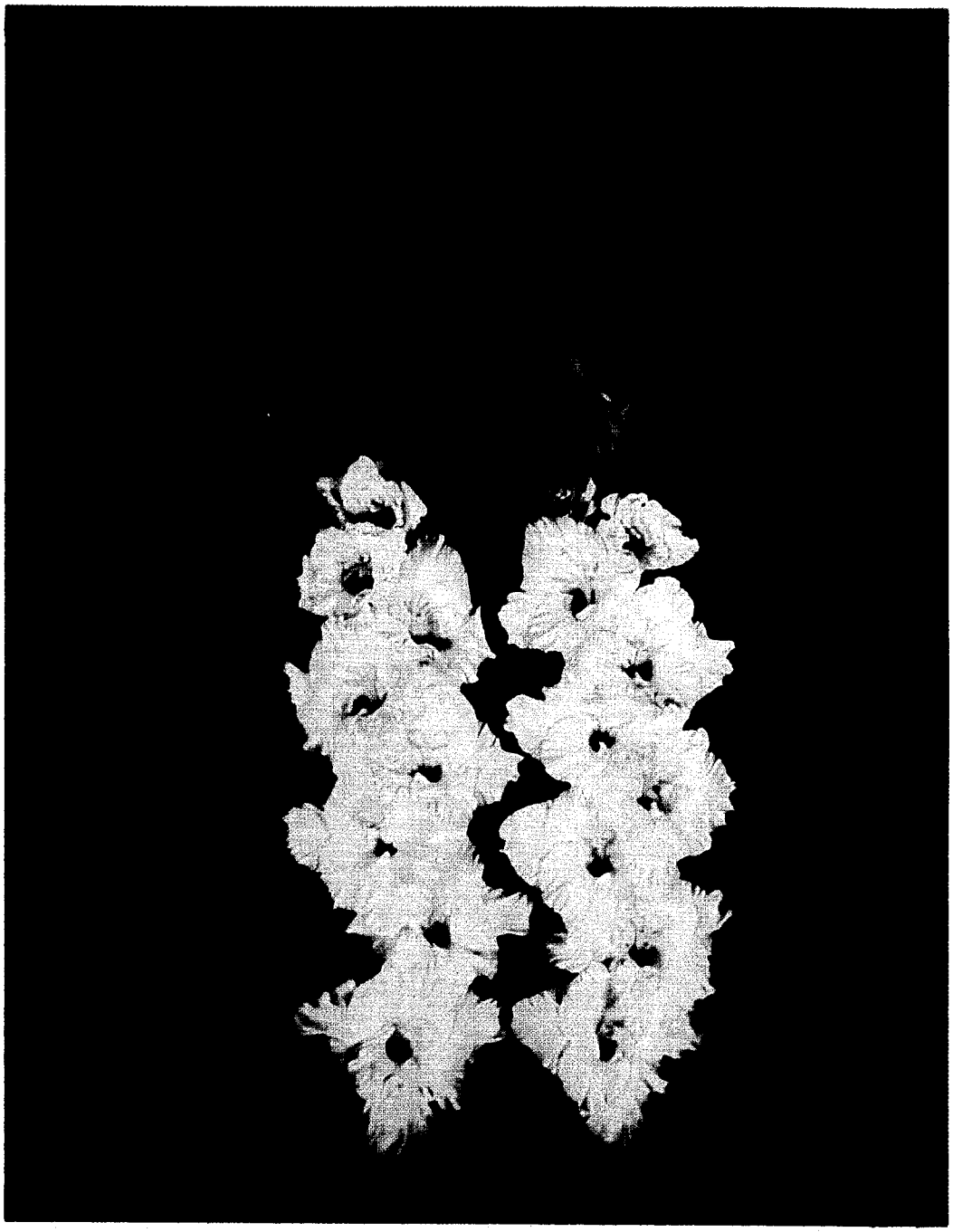
Inventor.
Carl Fischer
By: Robb & Robb
Attorneys.

United States Patent Office

Plant Pat. 2,361
Patented Feb. 11, 1964

2,361
GLADIOLUS PLANT

Carl Fischer, St. Charles, Minn., assignor to Imperial Flowers Limited, Leamington, Ontario, Canada, a corporation of Canada Filed Dec. 18, 1962, Ser. No. 245,629
1 Claim. (Cl. Plt.—85)

The present invention relates to a new and distinct variety of gladiolus plant which was originated by me by crossing the variety known as "Friendship" (unpatented) with the variety known as "Beauty's Blush" (unpatented), the former being the seed parent and the latter being the pollen parent. This cross was made by me by manual cross-pollination in my breeding fields at St. Charles, Minnesota, as a part of a breeding program seeking to obtain new and improved gladiolus varieties.

As the result of this particular cross, I have produced a new gladiolus variety which is endowed with a unique combination of outstanding features which distinguishes it from its parents, as well as from all other varieties of which I am aware, as evidenced by the following characteristics which are present therein:

(1) Robust, vigorous and healthy habits of growth;
(2) Intense ruffling of the flower petals;
(3) Heavy flower petal substance;
(4) Good resistance to hot and cold temperatures;
(5) A distinctive and attractive Sulphur Yellow general color tonality of the flowers, with the deepest color appearing in the flower throats; and
(6) Consistency of performance.

My new variety resembles the variety "Lorelei" (unpatented) more than any other, but differs principally therefrom by being more rugged and more disease resistant, a habit of growth that is not as straight or stiff, rounder and more intensely ruffled flower petals, flatter open flowers and better temperature tolerance.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows two typical specimen flower spikes of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely rugged; prolific propagator; average height ranges from about 60 inches to 62 inches.

Blooming habit: Early mid-season bloomer in the Northern latitudes of the United States; comes into bloom from large bulbs in from about 75 to 80 days.

Stems: Tall; willowy.
*Diameter at base.*—About ⅜ inch.
*Color (just above bulb).*—White.

Foliage: Healthy; slender; upright; leaves average from about 36 inches to 38 inches tall and about 1½ inches wide. Color—green.

Disease resistance: Unusually resistant to Fusarium yellows, Sclerotina dry rot and Septoria leaf spot, as determined by comparison with other varieties grown in my fields near St. Charles, Minnesota, in irrigated black loam soil.

Corms (bulbs): Round; plump; average diameter ranges from about 2 inches to 2½ inches; well husked, with husks being heavy and rough. Color of flesh—Amber Yellow, Plate 505/1.

*Flower*

Spike: Tall; flowerhead averages about 27 inches long; bears 17 or 18 buds, with 7 or 8 opening at once and with 5 or 6 additional buds showing color.

Bud:
*Size.*—From about 2½ inches to 3 inches long when opening.
*Opening.*—Opens very well; 5 or 6 buds show color at one time.

Flower:
*Arrangement.*—Florets are semi-formally arranged on the stem and usually all face forward.
*Size.*—Lower florets average from about 4¾ inches to 5 inches in diameter, with upper florets being progressively smaller.
*Form.*—Florets are very round; very ruffled; very heavy substance.
*Keeping qualities.*—Keeps very well.

Petals:
*Shape.*—Round; ruffled; recurved; some are needle-pointed.
*Size.*—Outer petals—about 2¼ inches wide. Lip petal—about 1½ inches wide.
*Aspect.*—Extremely heavy substance; smooth and leathery surface, with some puckering in flower throats.
*Fragrance.*—Distinct; sweet.
*Color.*—From Sulphur Yellow, Plate 1/3 to Sulphur Yellow, Plate 1/2, with deepest shade in flower throats; very faint rose colored line at calyx.

*Reproductive Organs*

Stamens: Color—faint rose color.
Pistil: Color—Sulphur Yellow.

I claim:

A new and distinct variety of gladiolus plant, substantially as herein shown and described, characterized particularly as to novelty by the unique combination of a robust, vigorous and healthy habit of growth, intense ruffling of the flower petals, heavy flower petal substance, good resistance to hot and cold temperatures, a distinctive and attractive Sulphur Yellow general color tonality of the flowers, with the deepest color in the flower throats, and consistency of performance.

No references cited.